United States Patent
Son et al.

(10) Patent No.: US 7,084,288 B2
(45) Date of Patent: Aug. 1, 2006

(54) ORGANOMETALLIC PRECURSOR FOR FORMING METAL FILM OR PATTERN AND METHOD OF FORMING METAL FILM OR PATTERN USING THE SAME

(75) Inventors: Hae Jung Son, Suwon-Shi (KR); Euk Che Hwang, Osan-Shi (KR); Sang Yoon Lee, Seoul (KR); Soon Taik Hwang, Seongnam-Shi (KR); Byong Ki Yun, Osan-Shi (KR)

(73) Assignee: Samsung Electronics Co., Ltd., Kyungki-Do (KR)

( * ) Notice: Subject to any disclaimer, the term of this patent is extended or adjusted under 35 U.S.C. 154(b) by 162 days.

(21) Appl. No.: 10/676,031

(22) Filed: Oct. 2, 2003

(65) Prior Publication Data

US 2004/0176623 A1    Sep. 9, 2004

(30) Foreign Application Priority Data

Mar. 4, 2003    (KR) .................... 10-2003-0013419

(51) Int. Cl.
C07F 15/02    (2006.01)
C07F 3/00    (2006.01)
C23C 16/00    (2006.01)

(52) U.S. Cl. ............................ 556/137; 556/7; 556/21; 556/118; 556/138; 427/248.1; 427/587; 106/1.26; 106/1.28; 106/1.29

(58) Field of Classification Search ............... 556/7, 556/21, 118, 137, 138; 106/1.26, 1.28, 1.29; 427/587, 248.1

See application file for complete search history.

(56) References Cited

U.S. PATENT DOCUMENTS

| | | | |
|---|---|---|---|
| 4,186,244 A | 1/1980 | Deffeyes et al. | 428/570 |
| 4,463,030 A | 7/1984 | Deffeyes et al. | 427/216 |
| 5,173,330 A | 12/1992 | Asano et al. | 427/558 |
| 5,882,722 A | 3/1999 | Kydd | 427/123 |
| 6,036,889 A | 3/2000 | Kydd | 252/512 |

OTHER PUBLICATIONS

Vogel et al., Angewandte Chemie International Edition in English, vol. 30, No. 3, pp. 303-304 (1991).*

(Continued)

*Primary Examiner*—Porfirio Nazario-Gonzalez
(74) *Attorney, Agent, or Firm*—Harness, Dickey & Pierce, PLC (57) ABSTRACT

The object of this invention is to provide an organometallic precursor for forming a metal film or pattern and a method of forming the metal film or pattern using the same. More particularly, the present invention provides an organometallic precursor containing a hydrazine-based compound coordinated with a central metal thereof, and a method of forming a metal film or pattern using the same. Further, the present invention provides a composition containing an organometallic compound and a hydrazine-based compound, and a method of forming a metal film or pattern using the same. Additionally, the present invention is advantageous in that a pure metal film or pattern is formed using the organometallic precursor or composition through a simple procedure without limiting atmospheric conditions at a low temperature, and the film or pattern thus formed has excellent conductivity and morphology. Therefore, the film is useful in an electronic device field including flexible displays and large-sized TFT-LCD.

14 Claims, 4 Drawing Sheets

OTHER PUBLICATIONS

K. Teng et al., "Liquid Ink Jet Printing with MOD Inks for Hybrid Microcircuits", IEEE Transactions on Components, Hybrids, and Manufacturing Technology, vol. CHMT-12, No. 4, Dec. 1987, pp. 545-549.

* cited by examiner

ORGANOMETALLIC PRECURSOR FOR FORMING METAL FILM OR PATTERN AND METHOD OF FORMING METAL FILM OR PATTERN USING THE SAME

This nonprovisional application claims priority under 35 U.S.C. § 119(a) to Patent Application No(s). 2003-13419 filed in KOREA on Mar. 4, 2003, which is(are) herein incorporated by reference.

BACKGROUND OF THE INVENTION

1. Field of the Invention

The present invention pertains, in general, to an organometallic precursor for forming a very pure metal film or pattern and a method of forming the metal film or pattern using the same. More particularly, the present invention relates to an organometallic precursor containing a hydrazine compound coordinating with a central metal thereof, and a method of forming a metal film or pattern using the same. Further, the present invention relates to a composition containing an organometallic compound and a hydrazine compound, and a method of forming a metal film or pattern using the same.

2. Description of the Related Art

A metal pattern to be formed on a substrate continues to get smaller in accordance with the recent trend of an increase in the degree of integration and a decrease in the size of electronic devices such as integrated circuits (IC) and Liquid crystalline displays. Usually, the metal pattern is formed on the substrate through a photolithography process using a photoresist. The photolithography process generally includes a) forming a metal layer on a substrate via a chemical vapor deposition process (CVD process), a plasma deposition process, or an electrical plating process, b) coating a photoresist on the metal layer, c) exposing the photoresist to UV-radiation under a photomask and d) developing photoresist layer to obtain a patterned photoresist layer, and e) etching the metal layer under the pattern of photoresist with, for example, a reactive ion-etching process to form a metal pattern on the substrate.

However, since the photolithography process involves many complicated steps and requires the use of a large amount of fine chemicals such as expensive photoresist compositions and etchants, it is undesirable in terms of cost and environmental protection. In the photolithography process, there are many steps, such as depositing and etching that should be conducted at a high temperature and/or high pressure, and thus, operational costs are also high. Also, metal vapor diffusion possibly occurring in the process when high temperature are employed often brings about deteriorations in the performance of an electronic device and defects in the device. Especially, for a flexible display or a TFT-LCD to achieve a high quality picture and a large-scaled screen, a technology is urgently required to be developed that can form a gate dielectric layer of high quality and a source/drain electrode region with low resistance. Thus, many studies have been made on the formation of a metal film or pattern through a simple procedure at a relatively low temperature.

As an alternative technology that can substitute for photolithography process, soft-lithography and ink-jet printing are attracting attention because they can form a fine pattern on a substrate with relatively simplified procedures and low operation costs. However, these two processes still have the problems that a film or a pattern must be heat-treated, or additionally oxidized or reduced at a high temperature in order for the film or pattern thus obtained to have lower resistivity. Therefore, when considering the materials currently used for the substrate, there remains a need to develop an ink which can form a metal pattern with high durability and high conductivity at a high resolution via a more simplified process requiring a low temperature.

IEEE Transactions on components Hybrids and Manufacturing Technology 12(4), 1987 ("Liquid ink-jet printing with MOD inks for hybrid microcircuits", Teng, K. F. and Vest, R. W.) discloses organometallic compounds that can be thermally decomposed at low temperatures and converted into metals or metal oxides, so called metallo-organic decomposition compounds (MOD compounds). Also, U.S. Pat. No. 5,882,722 discloses a technology of forming a metal film or pattern using the MOD compounds. However, this technology is disadvantageous because of the problem that the metal film or pattern thus formed is apt to be molten before thermal-decomposition so it is very difficult to secure the required thickness of the metal film or pattern while obtaining a conductivity of the metal film or pattern that is high. To avoid this problem, use of a multi-coating layer has been proposed as an alternative, but it is not good because coating multi-layers entails not only many complicated steps but also high costs. U.S. Pat. No. 5,173,330 discloses a method using organo-metal precursors to form a metal thin film or nuclei that is normally used in an electrolytic plating process but this method is undesirable because of low conductivity of the obtained film or pattern. Further, U.S. Pat. Nos. 4,186,244 and 4,463,030 disclose a process of forming a metal film by using silver (Ag) powder and a surfactant wrapping the silver powder at a low temperature. However, this process is disadvantageous in that, after formation, the metal film should be exposed to a temperature of 600° C. or higher in order to remove the surfactant. If the metal film is not exposed to this high temperature, the specific resistivity of the metal film becomes undesirably increased because of organic materials remaining on the metal film.

Additionally, U.S. Pat. No. 6,036,889 discloses a process of forming a relatively highly conductive metal pattern with a specific resistivity of about 3.0 μΩcm−1 on a polymer substrate at the low temperatures of 350° C. or lower using a mixture of MOD compounds, metal flakes, and metal colloid. In this process, the MOD compounds play a role in lowering the required temperature for heat treatment, while aiding the coating of composition on the substrate, and the metal flakes promote the solidification of a precursor to prevent the MOD compounds from being melted before the formation of the metal pattern. This process overcomes the conventional problems by using a mixture of many compounds wherein one compound helps avoid the problems of other compounds so it can be possible to form the metal pattern with excellent properties. However, there is a limitation in improving the properties of the metal pattern because the fundamental problems in the prior art are not solved completely and the content of each compound is limited. Hence, it is impossible for this process to form a metal film or pattern with a high conductivity corresponding to a pure metal at a temperature of 250° C. or lower.

Therefore, there remains a need to develop a method of forming a metal film or pattern, wherein the film or pattern has high conductivity corresponding to that of a pure metal. Moreover, a simple procedure is desired that uses a relatively low temperature wherein the thickness of the metal film can be controlled successfully.

The present inventors have conducted extensive studies on this need and, as a result of the study, have developed a method of forming a highly conductive metal film or pattern through a simple procedure at a relatively low temperature, wherein, by treating i) an organometallic precursor compound containing as a ligand a specific compound with high reducing ability, or ii) a composition comprising the specific compound and an organometallic compound at a low temperature of 400° C. or lower, preferably 250° C. or lower, a central metal of the organometallic precursor compound or the composition is reduced with the decomposition of organic compounds. Through this method, a highly conductive metal film or pattern with specific resistivity of 2.5 to 3.0 μΩcm−1 can be formed.

SUMMARY OF THE INVENTION

Accordingly, it is an object of the present invention to provide a method of forming a highly conductive metal film or pattern at a relatively low temperature through a simple procedure.

One aspect according to the present invention to achieve the object is related to an organometallic precursor for forming a metal film or pattern, represented by the following Formula 1:

$$L_n M_m L'_p X_q \qquad \text{Formula 1}$$

{wherein,

M is a transition metal; L' is a neutral ligand;

X is an anion that may coordinate the transition metal;

m is an integer of 1 to 10, provided that when m is two or more, each M may or may not be same as each other;

p is an integer of 0 to 40, and q is an integer of 0 to 10, provided that when p or q is two or higher, L' s or Xs are independently identical or different with one another, and p and q are not 0 at the same time; and L is a hydrazine compound coordinating the transition metal, represented by the following Formula 2:

$$R_1 R_2 NNR_3 R_4 \qquad \text{Formula 2}$$

[wherein,

R1, R2, R3 and R4 are independently hydrogen; alkyl or aryl of 1 to 20 carbon atoms having substitution groups; or provided that the substitution groups are selected from the group consisting of halogen groups including F, Cl, Br or I, amine groups, hydroxyl groups, —SH(sulfhydryl) groups, cyano groups, sulphonic acid groups (SO$_3$H), R$_6$S—, R$_6$O— (R$_6$ is an alkyl or aryl group containing 1 to 20 carbons), and nitrile groups, and R$_5$ is R', R'$_2$N, or R'O (R' is hydrogen, or an alkyl or aryl group containing 1 to 20 carbons)]; and n is an integer of 1 to 40, provided that when n is two or more, Ls are independently identical or different with one another}.

Furthermore, the other aspect of the present invention is related to a composition for forming a metal film or pattern, which comprises a hydrazine compound represented by the Formula 2 and an organometallic compound represented by the following Formula 3:

$$M_m L'_p X_q \qquad \text{Formula 3}$$

{wherein,

M is a transition metal; L' is a neutral ligand;

X is an anion that can coordinate the transition metal;

m is an integer of one to ten, provided that when m is two or more, each M may or may not be same as each other; and p is an integer of 0 to 40, and q is an integer of 0 to 10, provided that when p or q is two or higher, L' s or Xs are independently identical or different with one another, and p and q are not 0 at the same time}.

Additionally, another aspect of the present invention is related to a method of forming a metal film or pattern using the organometallic precursor or composition.

BRIEF DESCRIPTION OF THE DRAWINGS

These and other aspects and advantages of the invention will become apparent and more readily appreciated from the following description of the preferred embodiments, taken in conjunction with the accompanying drawings of which:

FIGS. 6A to 6C are microphotographs of a metal pattern formed by using UV from the organometallic precursor according to the present invention.

DESCRIPTION OF THE PREFERRED EMBODIMENTS

A more detailed description of the present invention will be given, below.

In formulas 1 and 3, a metal M is preferably selected from the group consisting of Ag, Au, Cu, Pd, Pt, Os, Rh, Co, Ni, Cd, Ir, and Fe, and more preferably, is selected from the group consisting of Ag, Au, and Cu.

An organometallic precursor according to the present invention comprises as a ligand, hydrazine compounds with an excellent reducing ability. Because of the presence of this hydrazine ligand, a decomposition temperature of the organometallic precursor can be lowered significantly and, at the same time, reduction is efficiently conducted only by heat-treating a metal film without additionally using a reducing agent after the formation of the metal film, thereby forming a very pure metal thin layer or film formulas.

In formulas 1 and 3, L', a ligand bonded to a metal, is an organic compound containing donor atoms such as N, P, As, O, S, Se, or Te. Preferably, L' is a compound having 20 or fewer carbons and the donor atoms. More preferably, L' is selected from the group consisting of amines; alcohols; phosphine, phosphite, and phosphine oxides; arsines; thiols; carbonyls; alkenes; alkynes; and arenes. Specific examples for L' include acetonitrile, isopropyl alcohol and propyl amine.

Additionally, in formulas 1 and 3, X is an anion that functions to electrically neutralize a metal compound, and may coordinate a metal atom. In particular, X is an anion including 20 or fewer carbons and at least one member selected from the group consisting of O, N, S, P, F, Cl, Br, I, Sb, B, As, Bi, Si, and Sn. Examples of X include OH—, CN—, NO2-, NO3-, halides (F—, Cl—,Br—, or I—), trifluoroacetate, isothiocyanate, tetraalkylborate (BR4-, R is methyl, ethyl, or phenyl), tetrahaloborate (BX4-, X is F or Br), hexafluorophosphate (PF6-), triflate (CF3SO3-), tosylate (Ts-), sulphate (SO42-), carbonate (CO32-), acetylacetonate, hydrazino benzoic acid (CO2C6H4NHNH2-), and trifluoroantimonate (SbF6-). Like the case of L containing a hydrazine group, when the anion contains a hydrazine group (for example CO2C6H4NHNH2-), the decomposition characteristics of the organometallic precursor can be improved.

Furthermore, in formulas 1 and 3, when n, p, or q is two or higher, L, L', or X may or may not be the same as each other, and when there are two or more metals, L, L', or X may be used as the ligand connecting the metals to each other.

Examples of an organometallic precursor compound expressed by Formula 1 include Ag(CF3COO)CH3CONHNH2, Ag(CF3COO)t-butylcarbazate, Ag(CF3COO)benzoichydrazide, Ag(BF4)CH3CONHNH2, Ag(SbF6)CH3CONHNH2, Ag(SO3CF3)CH3CONHNH2, and Ag(NO3)CH3CONHNH2.

Examples of hydrazine compound expressed by the Formula 2 include acetic hydrazide, t-butylcarbazate and benzoichydrazide.

As well, examples of the organometallic compound expressed by Formula 3 include Ag(CF3COO), Ag(C4F7COO), Ag(SbF6), Ag(SO3CF3), Ag(BF4) and AgNO3.

The organometallic precursor of Formula 1 can be prepared by the following stepts: After the organometallic compound of Formula 3 is dissolved in a predetermined solvent, a solution of hydrazine compound of Formula 2 is added to the organometallic compound drop by drop, and agitated at room temperature. The solvent is then removed from the resulting mixture to produce an organometallic compound of Formula 1. Non-limiting, illustrative examples of the solvent include acetonitrile, isopropyl alcohol, and methanol. Also, the solutions of the organometallic compound of Formula 3 and the hydrazine compound of Formula 2 can be prepared from the same or different solvents.

The composition of the present invention, comprising the hydrazine compound of Formula 2 and the organometallic compound of Formula 3, can be prepared by dissolving each of the compounds in acetonitrile, isopropyl alcohol, or methanol, and then mixing them with each other at room temperature.

By using the organometallic precursor of Formula 1 or the composition comprising the hydrazine compound of Formula 2 and the organometallic compound of Formula 3, a very pure metal film or pattern with high conductivity can be produced by a simple procedure at a relatively low temperature.

In particular, the organometallic precursor or composition is directly coated on a substrate, or is coated on a substrate after the organometallic precursor or composition is dissolved in a predetermined organic solvent, and the coating of organometallic precursor or composition is then heat-treated at a maximum of 400° C., but preferably 250° C. or lower, to reduce and decompose the organometallic compound to form a very pure metal film. In the case of a pattern formation, an organometallic precursor solution or a composition solution coated on the substrate is partially heat-treated and the heat-treated portions are developed by a solvent to form the desired pattern. For example, the partial heat-treatment can be carried out by UV-irradiation under a photomask, or by direct-irradiation with a laser beam or an e-beam.

Non-limiting, illustrative examples of a solvent that can be used to dissolve the organometallic precursor or the composition according to the present invention, or that can be used in a development step after the formation of the pattern include nitriles such as acetonitrile, propionitrile, pentanenitrile, hexanenitrile, heptanenitrile, and isobutylnitrile; aliphatic hydrocarbons such as hexane, heptane, octane, and dodecane; aromatic hydrocarbons such as anisole, mesitylene, and xylene; ketones such as methyl isobutyl ketone, 1-methyl-2-pyrrolidinone, cyclohexanone, and acetone; ethers such as tetrahydrofuran, diisobutyl ether, and isopropyl ether; acetates such as ethyl acetate, butyl acetate, and propylene glycol methyl ether acetate; alcohols such as isopropyl alcohol, butyl alcohol, hexyl alcohol, and octyl alcohol; inorganic solvents; and a mixture thereof.

Examples for the substrate used in the present invention, is not limited to, but can be selected from the group consisting of inorganic materials such as silicone or glass substrate, organic materials such as plastic substrate and composite materials that are composed of organic and inorganic materials.

Non-limiting, illustrative examples of a coating method according to the present invention include a spin coating, a roll coating, a deep coating, a spray coating, a flow coating, and a screen printing. Preferably, the spin coating can be used.

Figure 1:
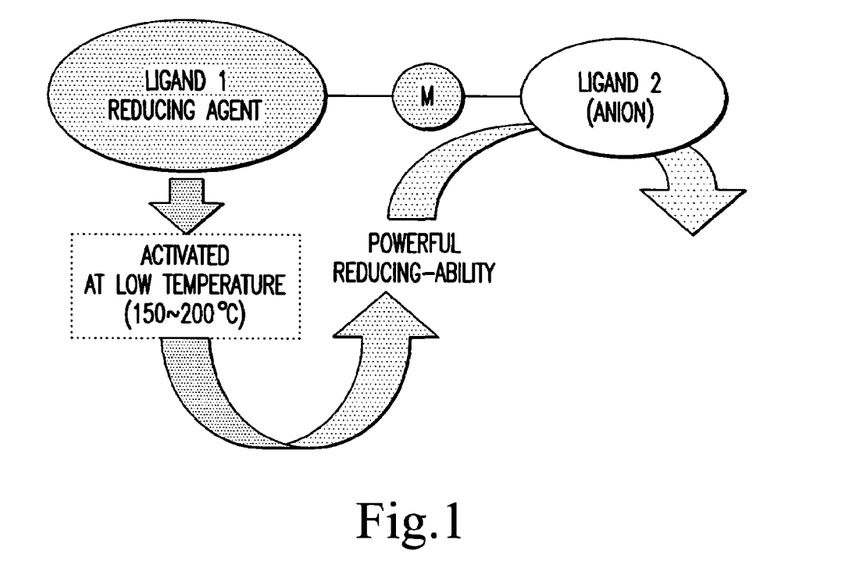
FIG. 1 is a flowchart schematically illustrating the production of a pure metal from an organometallic precursor according to the present invention.

Then, the coating of the organometallic precursor or the composition on the substrate is heat-treated at a maximum of 400° C., preferably at a temperature of 250° C. or lower, more preferably at a temperature of 150 to 250° C. According to the present invention, the organometallic precursor contains, as a ligand, the hydrazine compound that has excellent reducing ability and is activated at a relatively low temperature so, when being subjected to the heat-treatment, the hydrazine ligand activated by the heat-treatment reduces a central metal and, at the same time, promotes the decomposition of the organometallic precursor, thereby an organic portion of the organometallic compound is decomposed and removed, and a pure metal portion is obtained (FIG. 1). Because of the introduction of a hydrazine compound as a ligand, reduction of the central metal can proceed efficiently without any other reducing agent and a temperature at which decomposition begins is significantly lowered, and thereby a heat treatment at a relatively low temperature can produce a highly conductive, pure metal film. As described above, the organometallic precursor of the present invention is simultaneously decomposed and reduced by the heat-treatment at a low temperature, so it is relatively easy for a coated film to have a desired thickness by controlling a concentration of the solution of the organometallic precursor. Thereby, conventional problems with controlling the film thickness, i.e. difficulties in securing the thickness of a coated film resulting from melting during the heat-treatment of MOD, is solved. Additionally, the composition of the present invention, wherein the hydrazine compound and organometallic compound do not even form a perfect coordinate compound because of steric hindrance, may lower the thermal decomposition temperature and facilitate the reduction reaction.

The heat-treatment may be conducted under a nitrogen atmosphere, a vacuum, or an air atmosphere. In the case of using the organometallic precursor or composition of the present invention, it is very advantageous that the very pure metal film with high conductivity forms irrespective of the atmospheric conditions. The morphology of the metal film thus obtained is excellent. Further, the heat-treatment can be performed in two or more steps, as being divided with a soft-baking process conducted at a temperature of 200° C. or lower (preferably, at a temperature of 100 to 150° C.), and an annealing process conducted at 200 to 400° C.

The organometallic precursor or composition according to the present invention can be applied to any known patterning process using heat and, especially, to soft lithography, to an imprinting, to an ink-jet printing, to a silk-screen, and to a direct patterning method with an electromagnetic wave (a laser beam, an e-beam, or UV).

The "soft lithography" includes a microcontact printing, a microtransfer printing, a micro molding in capillary (MIMIC), and a solvent-assistance micromolding. In this process, patterns of organic compounds or organic materials are transferred onto a substrate using an elastomeric stamp or mold with fine patterns (Younan Xia et al., Angew. Chem. Int. Ed. 1998, 37, 550–575). In the soft lithography process, a self-assembled monolayer of specific compounds is formed on a substrate by a contact printing process, and a fine structure is formed by an embossing process (imprinting process) and a replica molding process. The soft lithography process using the organometallic precursor or composition of the present invention includes the steps of i) preparing a mold or a stamp with fine patterns; ii) injecting or coating the organometallic precursor solution of the Formula 1 or the composition solution containing the hydrazine compound and organometallic compound of Formulas 2 and 3 into the mold or on the stamp, transferring the resulting solution onto a predetermined substrate, and heat-treating the solution on the substrate. The mold or stamp preferably consists of polydimethylsilane (PDMS).

A better understanding of the present invention may be obtained in light of the following examples which are set forth to illustrate, but are not to be construed to limit the present invention.

PREPARATION EXAMPLES OF ORGANOMETALLIC PRECURSOR COMPOUND

All compounds used in the present invention were synthesized under a nitrogen atmosphere without humidity or oxygen according to Schlenk technology or Glove box technology.

1) Synthesis of $Ag(CF_3COO)CH_3CONHNH_2$

In a 50 mL round Schlenk flask, 2.209 g (10.000 mnol) of silver trifluoroacetate (Ag(CF3COO)) was dissolved in 20 mL of acetonitrile (MeCN), and, to the resulting solution, 0.781 g (10.000 mmol) of acetichydrazide (CH3CONHNH2) dissolved in acetonitrile was added dropwise. The resulting mixture was agitated at room temperature for 15 minutes, and the solvent was evaporated under a reduced pressure over three to four hours. The 1H-NMR spectrum result of the resulting product is shown below.

1H-NMR(CD3CN, ppm): 9.27 [s, 1H, —CH3CON—H]], 4.79 [s, 2H, —NHN—H2], 1.83 [s, 3H, —NHCOCHCH3]

2) Synthesis of Ag(CF3COO)t-butylcarbazate

The procedure of preparation example 1 was repeated to produce Ag(CF3COO)t-butylcarbazate, except that 1.322 g (10.000 mmol) of t-butylcarbazate was used instead of acetichydrazide. The 1H-NMR spectrum result of Ag(CF3COO)t-butylcarbazate is shown below.

1H-NMR(CD3CN, ppm): 7.72 [s, 1H, —OCON—H]], 4.59 [s, 2H, —NHN—H2], 1.44 [s, 9H, —NHCOOC(CH3)3]

3) Synthesis of $Ag(CF_3COO)benzoichydrazide$

The procedure of preparation example 1 was repeated to produce Ag(CF3COO)benzoichydrazide, except that 1.362 g (10.000 mmol) of benzoichydrazide was used instead of acetichydrazide. The 1H-NMR spectrum result of Ag(CF3COO)benzoichydrazide is shown below.

1H-NMR(CD3CN, ppm): 9.10[s, 1H, —PhCON—H]], 4.61[s, 2H, —NHN—H2], 7.77[d, 2H, —PhCO/2,6H], 7.44 [m, 2H, —PhCO/3,4,5H]

4) Synthesis of $Ag(BF_4)CH_3CONHNH_2$

The procedure of preparation example 1 was repeated to produce Ag(BF4)CH3CONHNH2 except that 1.947 g (10.000 mmol) of silver tetrafluoroborate (AgBF4) was used instead of silver trifluoroacetate. The 1H-NMR spectrum result of Ag(BF4)CH3CONHNH2 is shown below.

1H-NMR(CD3CN, ppm): 7.94[s, 1H, —CH3CON—H]], 4.24[s, 2H, —NHN—H2], 1.83[s, 3H, —NHCOCH3]

5) Synthesis of $Ag(SO_3CF_3)CH_3CONHNH_2$

The procedure of preparation example 1 was repeated to produce Ag(SO3CF3)CH3CONHNH2, except that 2.569 g (10.000 mmol) of silver trifluoro methane sulfonate Ag(SO3CF3) was used instead of silver trifluoroacetate. The 1H-NMR spectrum result of Ag(SO3CF3)CH3CONHNH2 is shown below.

1H-NMR(CD3CN, ppm): 8.03[s, 1H, —CH3CON—H]], 4.42[s, 2H, —NHN—H2], 1.82[s, 3H, —NHCOCH3]

6) Synthesis of $Ag(SbF_6)CH_3CONHNH_2$

The procedure of preparation example 1 was repeated to produce Ag(SbF6)CH3CONHNH2, except that 3.436 g (10.000 mmol) of silver hexafluoroantimonate (Ag(SbF6)) was used instead of silver trifluoroacetate. The 1H-NMR spectrum result of Ag(SbF6)CH3CONHNH2 is shown below.

1H-NMR(CD3CN, ppm): 7.82[s, 1H, —CH3CON—H]], 4.32[s, 2H, —NHN—H2], 1.82[s, 3H, —NHCOCH3]

7) Synthesis of $Ag(NO_3)CH_3CONHNH_2$

The procedure of preparation example 1 was repeated to produce Ag(NO3)CH3CONHNH2, except that 1.699 g (10.000 mmol) of silver nitrate (AgNO3) was used instead of silver trifluoroacetate. The 1H-NMR spectrum result of Ag(NO3)CH3CONHNH2 is shown below.

1H-NMR(CD3CN, ppm): 9.04[s, 1H, —CH3CON—H], 4.92[s, 2H, —NHN—H2], 1.89[s, 3H, —NHCOCH3]

PREPARATION EXAMPLE OF COMPOSITION CONTAINING ORGANOMETALLIC COMPOUND AND HYDRAZINE COMPOUND 2.209 g (10.000 mmol) of silver trifluoroacetate (Ag (CF3COO)) was dissolved in 5 mL of acetonitrile in a vial with a volume of 20 mL, and 0.736 g (10.000 mmol) of (CH3)3CO CONHNHCO2C(CH3)3 dissolved in acetonitrile (5 mL) was added dropwise to a silver trifluoroacetate solution to produce a 1 M precursor sample.

Examples 1 to 8

Formation of Metal Films

A metal film was formed using the organometallic precursor compounds of Preparation Examples 1) to 7) and a composition comprising an organometallic compound and a hydrazine compound, and physical properties of the metal film were evaluated.

In detail, an organometallic compound as described in Table 1 was dissolved in a predetermined solvent, spin-coated on a glass substrate, soft-baked at 150° C. under a vacuum, and annealed at 250° C. to form the metal film. The thickness and resistivity of the metal film were measured using an alpha-step and a four-point probe.

Among the organometallic precursor compounds produced in Preparation Examples 1) to 7), the metal films produced by using Ag(CF3COO)CH3CONHNH2 and Ag(CF3COO)t-butylcarbazate had excellent solubility to acetonitrile and 2-propanol. All the metal films had excellent appearance (when being observed by the naked eye) and high conductivity irrespective of the kinds of solvents used. Particularly, the metal film from Ag(BF4)CH3CONHNH2 had excellent adhesion to the glass substrate. Additionally, Ag(CF3COO)benzhydrazide showed poor solubility in acetonitrile, so a 1:1 mixture of acetonitrile and acetone was used as a solvent.

TABLE 1

| [1]Ex. | Compound | Solvent | [2]Conc. | [3]Resist. | [4]Thick. |
|---|---|---|---|---|---|
| 1 | Ag(CF$_3$COO)CH$_3$CONHNH$_2$ | MeCN | 1.5M | 2.5 | 2000 |
| 2 | Ag(CF$_3$COO)t-butylcarbazate | MeCN | 1.5M | 3.3 | 1853 |
| 3 | Ag(CF$_3$COO)benzoichydrazide | Acetone:MeCN (1:1) | 1.0M | 256 | 2053 |
| 4 | Ag(BF$_4$)CH$_3$CONHNH$_2$ | MeCN | 1.5M | 10.2 | 2053 |
| 5 | Ag(SO$_3$CF$_3$)CH$_3$CONHNH$_2$ | MeCN | 1.5M | 113 | 3010 |
| 6 | Ag(SbF$_6$)CH$_3$CONHNH$_2$ | MeCN | 1.5M | 120 | 2200 |
| 7 | Ag(NO$_3$)CH$_3$CONHNH$_2$ | MeCN | 1.5M | 4 | 2005 |
| [5]Comp. | Ag(CF$_3$COO)/(CH$_3$)$_3$COCONHNHCO$_2$C (CH$_3$)$_3$ | MeCN | 1.0M | 5.2 | 1950 |

[1]Ex.: Preparation examples
[2]Conc.: Concentration
[3]Resist.: Resistivity ($\mu\Omega$ cm$^{-1}$)
[4]Thick.: Thickness (Å)
[5]Comp.: Composition

Example 9

Figure 2:
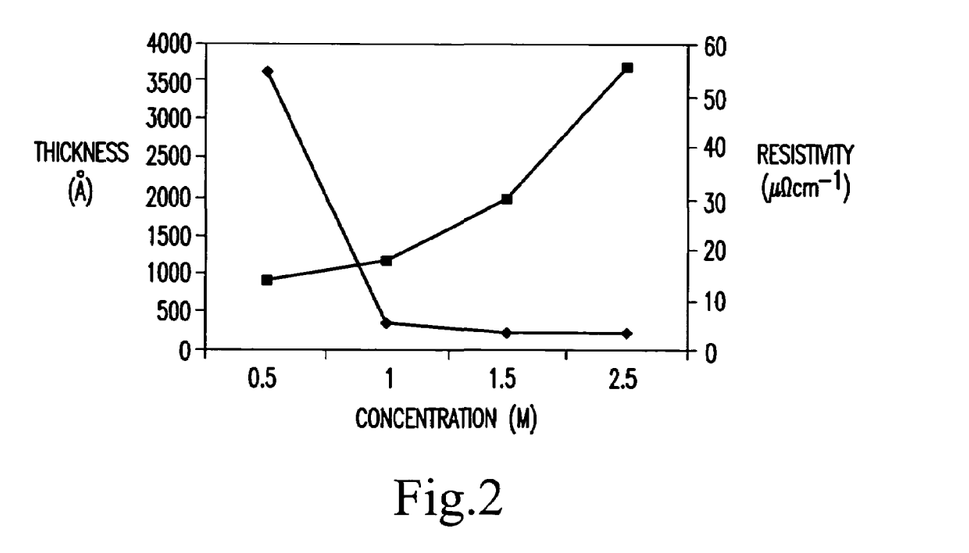
FIG. 2 is a graph showing the changes in thickness and resistivity of a metal thin film in relation to changes in a concentration of an organometallic precursor solution according to the present invention.
Figure 3:
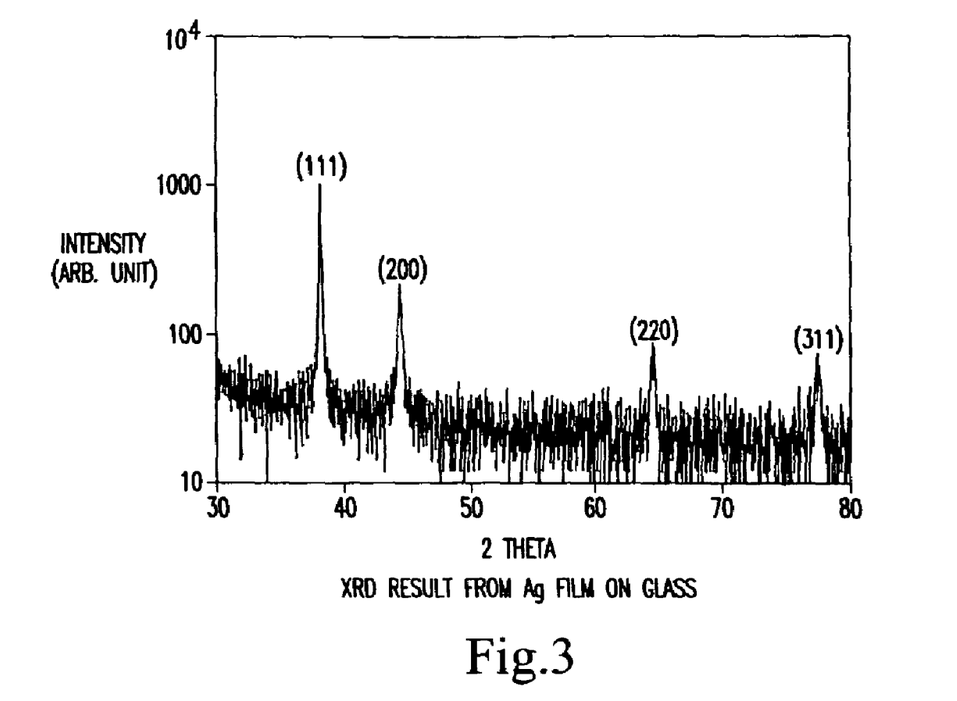
FIG. 3 is an X-ray diffraction spectrum of the metal thin film formed using the organometallic precursor solution according to the present invention.
Figure 4:
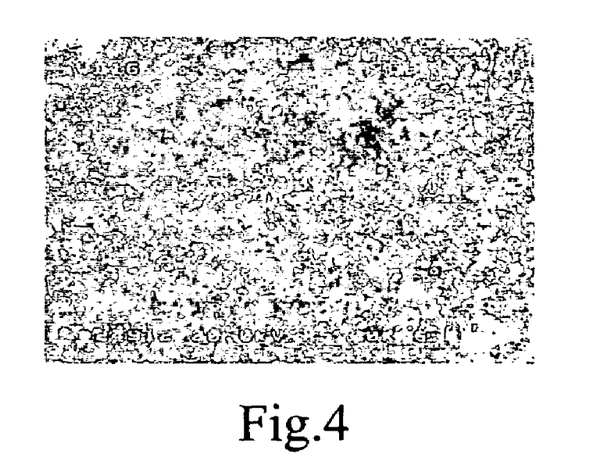
FIG. 4 is a SEM picture illustrating morphology of a surface of the metal thin film according to the present invention.

Changes in Physical Properties of a Metal Thin Film with the Increase of a Concentration of a Precursor Solution Ag(CF3COO)CH3CONHNH2 produced in preparation Example 1 was diluted using isopropyl alcohol in a predetermined concentration, and a metal thin film was formed and the thickness and resistivity of the metal thin film thus obtained were determined under the same conditions as Examples 1 to 8. The results are illustrated in FIG. 2. From FIG. 2, it can be seen that the thickness proportionally increased with concentration, and specific resistivity decreased to 2.5 $\mu\Omega$cm−1 at 1 M and, three was no change with the increase in concentration above 1 M. The metal thin film produced at 1.5 M was analyzed using an X-ray diffraction (XRD) analyzer and a scanning electronic microscope (SEM), and the results are illustrated in FIGS. 3 and 4. From the 2 θ values of FIG. 3, it can be seen that a silver polycrystal is formed.

Example 10

Figure 5:
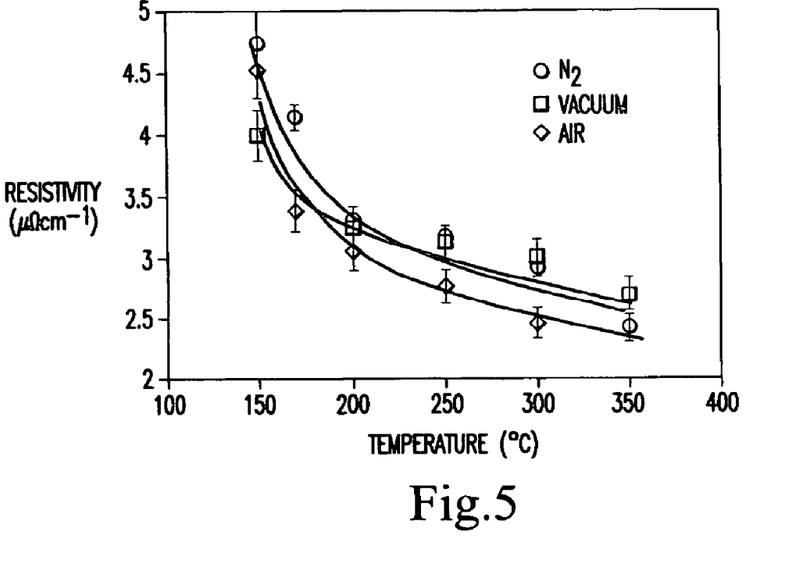
FIG. 5 is a graph showing changes in the resistivity of the metal thin film in accordance to atmospheric conditions.

Variation of Physical Properties of a Metal Thin Film under Various Atmospheres Ag(CF3COO)CH3CONHNH2 prepared in Preparation Example 1 was diluted to a concentration of 1.5 M using isopropyl alcohol, spin-coated on a substrate, and heat-treated under a nitrogen (N2) atmosphere, an air atmosphere, and a vacuum. The heat-treatment was conducted in such a way that Ag(CF3COO)CH3CONHNH2 was soft-baked at 150° C., and annealed at 200° C., 250° C., 300° C., and 350° C. to produce thin films. Resistivity of each thin film was measured, and the results are illustrated in FIG. 5. From FIG. 5, it can be seen that resistivity is related to temperature, but not atmospheric conditions.

Example 11

Pattern Formation by Using UV

Figure 6A:
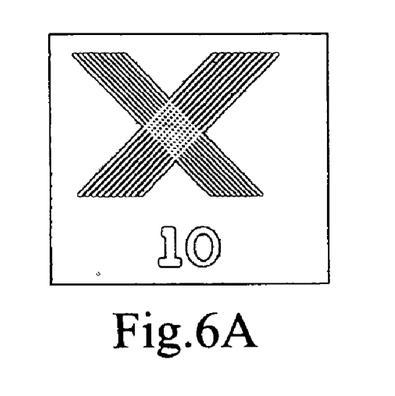
Figure 6B:
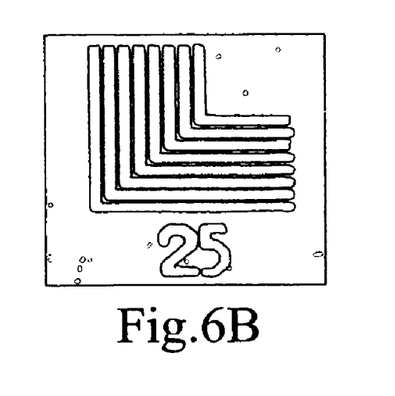
Figure 6C:
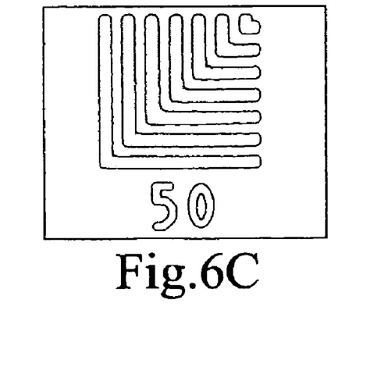

Ag(CF3COO)CH3CONHNH2 prepared in Preparation Example 1 was diluted to a concentration of 1.5 M with isopropyl alcohol, and spin-coated on a glass substrate. Under a mask having a predetermined pattern, the coating of Ag(CF3COO)CH3CONHNH2 was exposed to UV-irradiation equipment emitting UV and heat (manufactured by Oriel Co., 1 KW, UV broad band), for five to ten minutes, and developed by isopropyl alcohol. The resulting patterns are illustrated in FIG. 6.

Example 12

Formation of Patterns According to a Microcontact Printing Process

Figure 7:
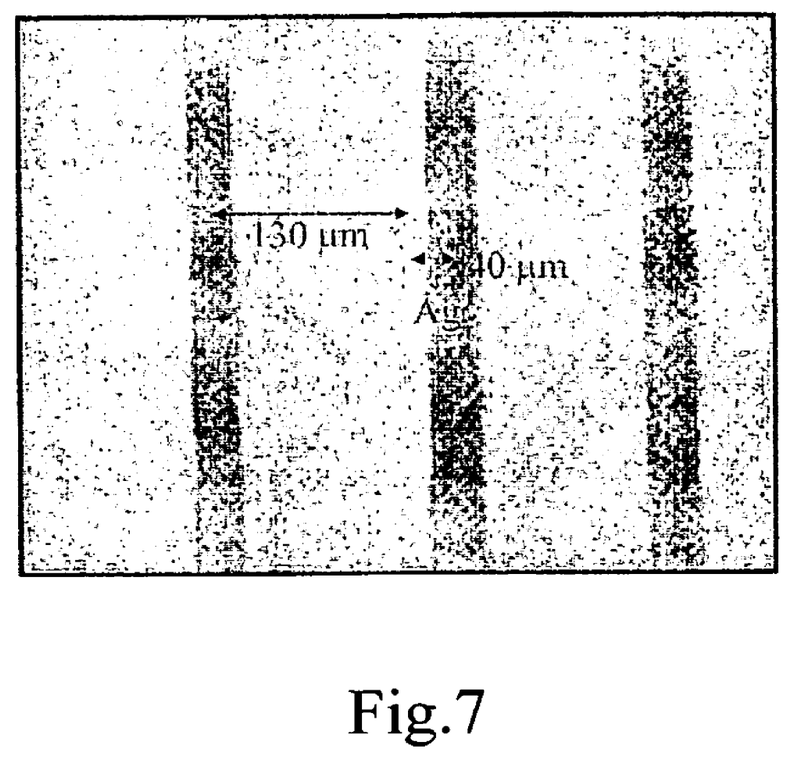
FIG. 7 is a microphotograph of a metal pattern formed from the organometallic precursor according to a soft lithography process.

After an octadecyltrichlorosilane (OTS) solution was coated on a polydimethylsiloxane (PDMS) stamp on which a pattern was formed, the coated solution was transferred on a predetermined glass substrate to form an OTS pattern. Ag(CF3COO)CH3CONHNH2 of Preparation Example 1 was diluted to a concentration of 1.5 M with isopropyl alcohol, and spin-coated on the above glass substrate with the OST solution pattern. The organometallic precursor compound was coated on only an OTS-free portion of the glass substrate. The resulting glass substrate was heat-treated at 200° C. for five minutes to form a silver (Ag) pattern on a portion of the glass substrate on which the organometallic precursor compound was coated (FIG. 7).

As described above, the present invention is advantageous in that a pure metal film or pattern is formed using an organometallic precursor or a composition of the present invention through a simple procedure at a low temperature, regardless of atmospheric conditions, and the film or pattern thus formed has high conductivity and excellent morphology. Therefore, the film prepared by the present invention is useful in an electronic device field including flexible displays and large-sized TFT-LCD.

Although a few preferred embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An organometallic precursor represented by the following Formula 1, for forming a metal film or pattern:

$L_n M_m L'_p X_q$  Formula 1

{wherein,

M is a metal selected from the group consisting of Ag, Au, Cu, Pd, Pt, Os, Rh, Ni, Cd, Ir, and Fe; L' is a neutral ligand;

X is an anion that may coordinate the transition metal;

m is an integer of 1 to 10, provided that when m is two or more, each M may or may not be the same as each other;

p is an integer of 0 to 40, and q is an integer of 0 to 10, provided that when p or q is two or higher, L's or Xs are independently identical or different with one another, and p and q are not 0 at the same time; and L is a hydrazine compound coordinating to the transition metal, represented by the following Formula 2:

$R_1 R_2 NNR_3 R_4$  Formula 2

[wherein, $R_1$, $R_2$, $R_3$ and $R_4$ are independently hydrogen; alkyl or aryl of 1 to 20 carbon atoms having at least one substitution group; or provided that the at least one substitution group is selected from the group consisting of halogen, amine, hydroxyl, —SH(sulfhydril), cyano, sulphonic acid ($SO_3H$), $R_6S$—, $R_6O$— ($R_6$ is an alkyl or aryl group containing 1 to 20 carbons), and nitrile, and $R_5$ is R', R'$_2$N, or R'O (R' is hydrogen, or an alkyl or aryl group containing 1 to 20 carbons)]; and n is an integer of 1 to 40, provided that when n is two or more, Ls are independently identical or different with one another}.

2. The organometallic precursor as set forth in claim 1, wherein L' is a ligand bonded to the metal, containing at least one donor atom having 20 or less carbons; and X is one or more anion that can coordinate a metal atom, the anion being selected from the group consisting of $OH^-$, $CN^-$, $NO_2^-$, $NO_3^-$, halide, trifluoroacetate, isothiocyanate, tetraalkylborate, tetrahaloborate, hexafluoro phosphate ($PF_6^-$), triflate ($CF_3SO_3^-$), tosylate ($Ts^-$), sulphate ($SO_4^{2-}$), carbonate ($CO_3^{2-}$), acetylacetonate, trifluoroantimonate ($SbF_6^-$), and an anion containing a hydrazine group.

3. The organometallic precursor as set forth in claim 1, wherein L' is at least one selected from the group consisting of amine; alcohol; phosphine; phosphite; phosphine oxide; arsine; thiol; carbonyl compound; alkene; alkyne; or arene.

4. The organometallic precursor as set forth in claim 1 or 2, wherein the organometallic precursor represented by the Formula 1 is $Ag(CF_3COO)CH_3CONHNH_2$, $Ag(CF_3COO)$t-butylcarbazate, $Ag(CF_3COO)$benzoichydrazide, $Ag(BF_4)CH_3CONHNH_2$, $Ag(SbF_6)CH_3CONHNH_2$, $Ag(SO_3CF_3)CH_3CONHNH_2$, or $Ag(NO_3)CH_3CONHNH_2$.

5. A composition for forming a metal film or pattern, which comprises a hydrazine compound represented by the following Formula 2 and an organometallic compound represented by the following Formula 3:

$R_1 R_2 NNR_3 R_4$  Formula 2

{wherein, $R_1$, $R_2$, $R_3$ and $R_4$ are independently hydrogen; alkyl or aryl of 1 to 20 carbon atoms having at least one substitution group; or provided that the at least one substitution group is selected from the group consisting of halogen, amine, hydroxyl, —SH(sulfhydril), cyano, sulphonic acid ($SO_3H$), $R_6S$—, $R_6O$— ($R_6$ is an alkyl or aryl group containing 1 to 20 carbons), and nitrile groups, and $R_5$ is R', R'$_2$N, or R'O (R' is hydrogen, or an alkyl or aryl group containing 1 to 20 carbons)}; and, $M_m L'_p X_q$  Formula 3

{wherein,

M is a transition metal; L' is a neutral ligand;

X is an anion that can coordinate the transition metal;

m is an integer of one to ten, provided that when m is two or more, each M may or may not be same as each other; and p is an integer of 0 to 40, and q is an integer of 0 to 10, provided that when p or q is two or higher, L's or Xs are independently identical or different with one another, and p and q are not 0 at the same time}.

6. A method of forming a metal film or pattern using a solution of the organometallic precursor of claim 1 or the composition of claim 5 with heat treatment.

7. The method as set forth in claim 6, wherein forming the metal film or pattern is performed by i) producing a pattern through a microcontact printing, a micro molding in capillary (MIMIC), an imprinting, an ink-jet printing, or a silk-screen, and ii) heating the pattern.

8. The method as set forth in claim 6, wherein the solution of organometallic precursor or the composition is prepared by dissolving the organometallic precursor or the composition in a solvent selected from the group consisting of nitriles; aliphatic hydrocarbons; aromatic hydrocarbons; ketones; ethers; acetates; alcohols; inorganic solvents; and a mixture thereof.

9. The method as set forth in claim 6, wherein the method comprises the steps of i) dissolving the organometallic precursor or the composition in a first solvent to produce a solution and coating the solution on a substrate; ii) partially heat-treating the solution coated on the substrate at 400° C. or lower; and iii) developing a heat-treated coating with a solvent to obtain the pattern.

10. The method as set forth in claim 9, wherein ii) the partial heat-treatment is conducted by using a laser beam or an electronic beam.

11. The method as set forth in claim 6, wherein the method comprises i) preparing a mold or a stamp with a fine pattern and ii) injecting or coating the organometallic precursor or the composition into the mold or on the stamp, transferring the organometallic precursor or composition onto a predetermined substrate, and heat-treating the transferred organometallic precursor or composition.

12. An organometallic precursor represented by the following Formula 1, for forming a metal film or pattern:

Formula 1

{wherein,

M is Co; L' is a ligand bonded to the metal comprising at least one donor atom selected from the group consisting of N, As, O, S, Se or Te or L' is a phosphite or phosphine oxide;

X is an anion that may coordinate the transition metal;

m is an integer of 1 to 10, provided that when m is two or more, each M may or may not be the same as each other;

p is an integer of 0 to 40, and q is an integer of 0 to 10, provided that when p or q is two or higher, L's or Xs are independently identical or different with one another, and p and q are not 0 at the same time; and L is a hydrazine compound coordinating to the transition metal, represented by the following Formula 2:

$R_1R_2NNR_3R_4$    Formula 2

[wherein, $R_1$, $R_2$, $R_3$ and $R_4$ are independently hydrogen; alkyl or aryl of 1 to 20 carbon atoms having at least one substitution group; or provided that the at least one substitution group is selected from the group consisting of halogen, amine, hydroxyl, —SH(sulfhydril), cyano, sulphonic acid ($SO_3H$), $R_6S$—, $R_6O$— ($R_6$ is an alkyl or aryl group containing 1 to 20 carbons), and nitrile, and $R_5$ is R', R'$_2$N, or R'O (R' is hydrogen, or an alkyl or aryl group containing 1 to 20 carbons)]; and n is an integer of 1 to 40, provided that when n is two or more, Ls are independently identical or different with one another}.

13. The organometallic precursor as set forth in claim 2, wherein the at least one donor atom is selected from the group consisting of N, P, As, O, S, Se, or Te; the halide is F⁻, Cl⁻, Br⁻, or I⁻; the tetraalkylborate is $BR_4^-$ wherein R is Me, Et or Ph; and the tetrahaloborate is $BX_4^-$, wherein X is F or Br.

14. The method as set forth in claim 8, wherein the solvent is selected from the group consisting of acetonitrile, propionitrile, pentanenitrile, hexanenitrile, heptanenitrile, isobutylnitrile, hexane, heptane, octane, dodecane, anisole, mesitylene, xylene, methyl isobutyl ketone, 1-methyl-2-pyrrolidinone, cyclohexanone, acetone, tetrahydrofuran, diisobutyl ether, isopropyl ether, ethyl acetate, butyl acetate, propylene glycol methyl ether acetate, isopropyl alcohol, butyl alcohol, hexyl alcohol, octyl alcohol and a mixture thereof.

* * * * *